United States Patent [19]

McSpadden

[11] 4,332,561
[45] Jun. 1, 1982

[54] DENTAL FILE

[75] Inventor: John T. McSpadden, Johnson City, Tenn.

[73] Assignee: Inventive Technology International, Inc., Johnson City, Tenn.

[21] Appl. No.: 263,406

[22] Filed: May 14, 1981

Related U.S. Application Data

[63] Continuation-in-part of Ser. No. 63,436, Aug. 3, 1979, Pat. No. 4,299,571.

[51] Int. Cl.³ ............................................. A61C 5/02
[52] U.S. Cl. ................................................ 433/102
[58] Field of Search ...................... 433/102; 408/714; 407/12, 13

[56] References Cited

U.S. PATENT DOCUMENTS

| | | | |
|---|---|---|---|
| 636,359 | 11/1899 | Schultz | 433/102 |
| 1,307,446 | 6/1919 | Kerr | 433/102 |
| 4,165,562 | 8/1979 | Sarfatti | 433/75 |
| 4,190,958 | 3/1980 | Martin et al. | 433/102 |
| 4,231,738 | 11/1980 | Riitano | 433/102 |

Primary Examiner—Robert Peshock
Attorney, Agent, or Firm—Luedeka & Fitch

[57] ABSTRACT

A dental file is disclosed which is particularly useful in endodontia for removing dead or damaged tissue from a curved tooth root canal. The file has a flexible tapered shank which has a cutting surface on its periphery and a pilot projecting from the tapered end of the file for guiding the shank along the curved root canal preventing the cutting surface near the end of the shank from gouging into the wall of the curved root canal or penetrating too far through the apical foramen of the root canal.

4 Claims, 8 Drawing Figures

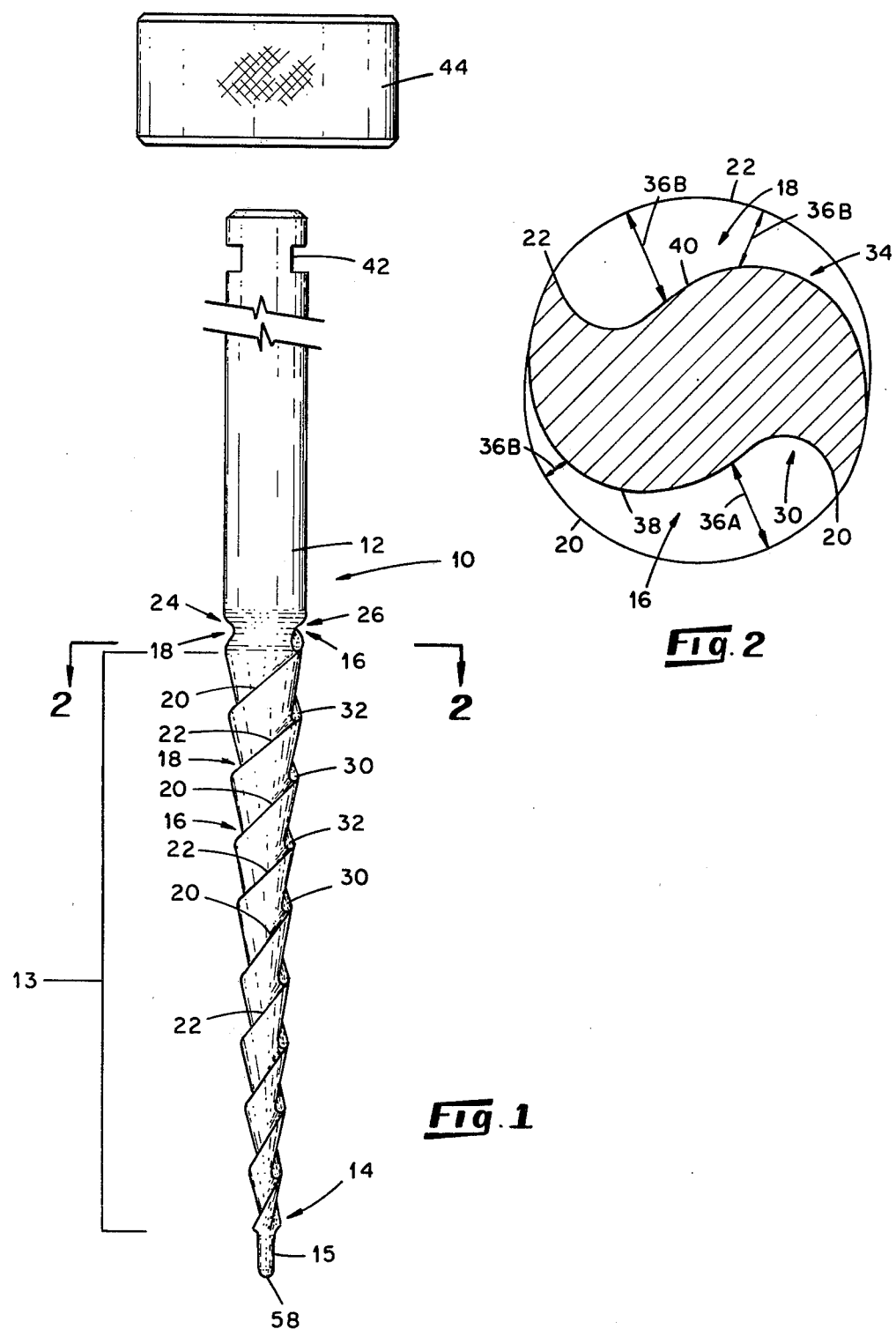

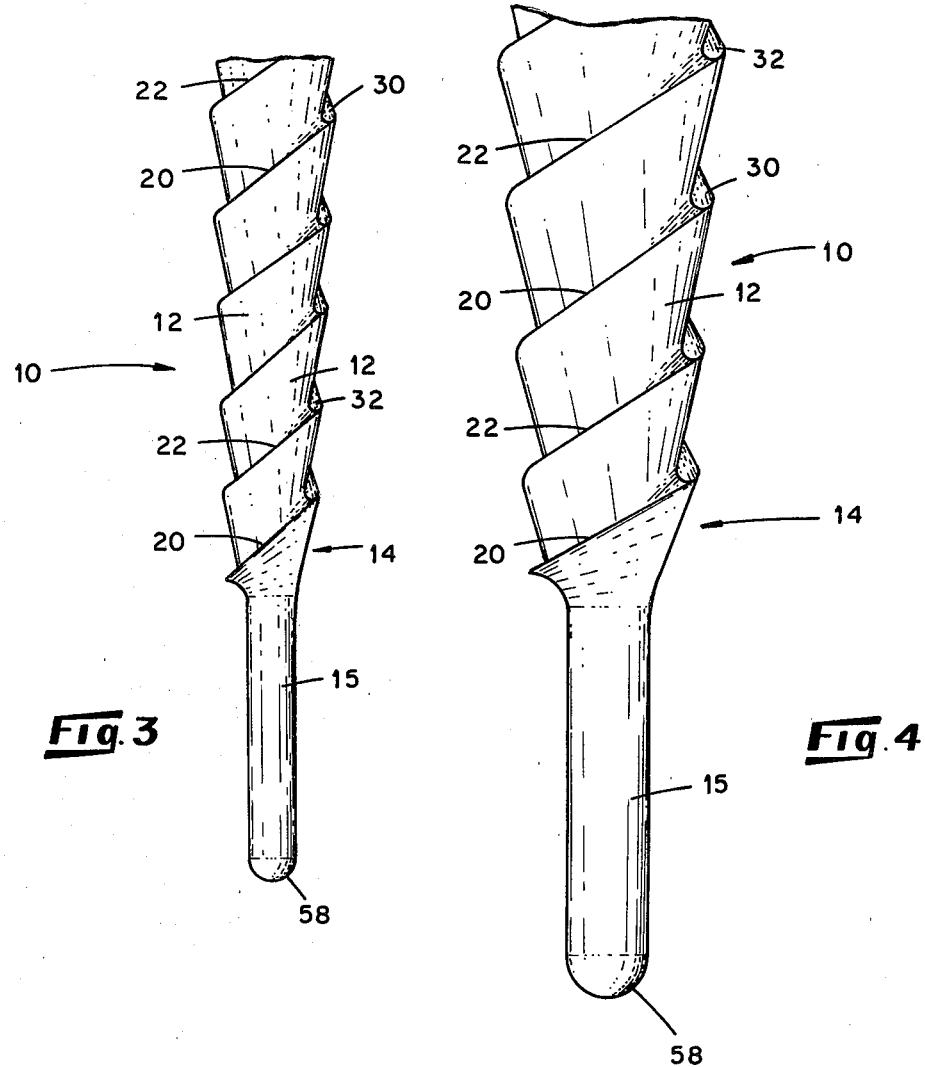

DENTAL FILE

This is a continuation in-part of my copending application Ser. No. 63,436, filed Aug. 3, 1979 and now U.S. Pat. No. 4,299,571 issued Oct. 10, 1981.

The present invention relates to the field of dental instruments and more particularly to files used in endodontia to remove dead or damaged material from a tooth root canal preparatory to filling the root canal.

In endodontia, one of the most delicate and precise operations is the removal of dead or damaged tissue from a tooth root canal, and the cleaning of the walls of the root canal before filling of the root canal with an appropriate material. Care must be taken not to cut too deeply into the walls of the root canal and unduly damaging the tooth structure, and not to penetrate too far into the apical foramen of the root canal unduly increasing its size and penetrating into the tooth supporting tissue.

Instruments called dental files are used to remove tissue from a root canal and properly clean the walls of the root canal. Typical dental files have a tapered shank with a working or cutting surface which cuts the tissue to be removed from the root canal as the file is moved in the root canal. These dental files can be manually manipulated by means of a hand grip affixed to one end of the file shank or the shank can be fitted into a power driven dental drill chuck or handpiece.

Typically, tooth root canals are not straight but are curved. As a dental file is moved in a curved tooth root canal, force vectors are exerted on the working surface near the end of the shank of the dental file by the tooth structure within the root canal and by the manipulating means. These force vectors create a force couple which bends the dental file into an arcuate configuration generally conforming to the curvature of the root canal. The component of this force couple exerted on the working surface of the shank is typically applied near the tapered end of the shank. Due to the modulus of elasticity of the material from which the dental file is fabricated, the dental file has a natural disposition to retain a straight configuration with the result that the end of the shank of the dental file exerts a counter force on the tooth structure against the concave surface of the curved root canal equal to the force vector on the end of the shank which causes it to bend. This counter-force will increase the cutting action of the working surface of the shank of the dental file and particularly of the end of the shank against the concave surface of the root canal. Under some conditions the dental file can cut too deeply into, or gouge the concave wall of the curved root canal forming what is sometimes referred to as a ledge, or even perforate through the tooth structure, and unduly damage the tooth structure.

The procedure, generally, is to start the removal operation with a small diameter file and to incrementally progress to larger diameter files until all of the dead or damaged material has been removed from the root canal and the walls of the root canal are properly cleaned. Due to the formation of a gouge or ledge in the concave wall of the curved root canal, each succeedingly larger file will move into the ledge created by the previous file and will be bent to a lesser extent. Thus, the curvature of the curved root canal will be continuously distorted or straightened from its original curvature. It is even possible that the ledge will be increased in size as succeedingly larger files are used to such an extent that a file penetrates through the tooth structure resulting in undue damage to the tooth structure. Furthermore, under some conditions the dental files can penetrate the apical foramen of the root canal increasing the size of the apical foramen as succeedingly larger diameter files are used causing undue damage to the tooth structure and possibly the tooth supporting tissue.

An object of the invention is to provide a set of increasingly sized dental files which will more truly follow the natural curvature of a tooth root canal and which will minimize the formation of ledges and minimize the chances of perforating the tooth structure.

Another object of the invention is to provide a set of increasingly sized dental files which will not readily increase the size of the apical foramen of the root canal.

These and other objects and advantages of the present invention will be recognized from the following description and figures in which:

FIG. 1 illustrates a dental file embodying various features of the present invention, the proportions of the dental file being somewhat distorted to clearly show structural features;

FIG. 2 is an enlarged cross-section taken in the direction of arrows 2—2 of FIG. 1;

FIG. 3 is an enlarged view of an end portion of a file one size, embodying various features of the present invention;

FIG. 4 is an enlarged view of an end portion of a file similar to that shown in FIG. 3, but of a larger size;

Figure 5:
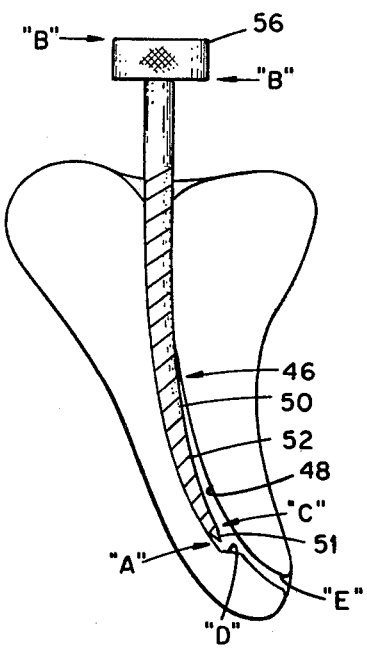
FIG. 5 illustrates a heretofore known file in use.

The illustrated embodiment shows a file particularly adapted for removing tissue from the root canal of a tooth which comprises a flexible shank tapered along at least part of its length and having a cutting surface formed in at least a portion of its tapered length and a generally cylindrical smooth walled pilot having a generally blunt end projecting coaxially from the tapered end of the shank.

As illustrated, the cutting surface formed in the shank comprises at least two oppositely disposed continuous helical flutes formed in at least a portion of the tapered length of the shank defining at least two oppositely disposed helical cutting edges. However, it should be clearly understood that the present invention can be used with a dental file formed with another type of cutting surface. For example, the present invention can be used with a file having its shank formed with diamond chips, or a dental file having one helical flute and cutting edge as the Hedstrom file.

Now with reference to the FIGS. 1, 2 and 3, the dental file, generally denoted as the numeral 10, has a flexible shank 12 tapered along at least a portion of its length 13 to a tapered end 14 and a pilot 15 projecting coaxially from the tapered end 14. A portion of the shank above the tapered portion is illustrated as being substantially cylindrical. Two continuous helical flutes 16 and 18 are formed in at least a portion 14 of the tapered length of the shank 12 defining two helical cutting edges 20 and 22 respectively.

The two continuous helical flutes are a first flute 16 and a second flute 18. The second flute 18 originates at a region, denoted as the numeral 24, 180° around the circumference of the shank 12 from the origination region, denoted as the numeral 26, of the first flute 16. Each of these flutes 16 and 18 is a continuous flute from its point of origin to the tapered end 14 of the shank 12.

The first continuous helical flute 16 defines a first sharp, continuous, helical cutting edge 20 and the second continuous helical flute 18 defines a second sharp, continuous, helical cutting edge 22. Each of these cutting edges 20 and 22 is generally directed upwardly or away from the tapered end 14 of the shank 12 as will be described below. Preferably, the cutting edges 20 and 22 number from about 0.1 to about 5.0 per millimeter of shank length.

As illustrated, the flutes 16 and 18 follow a right-handed twist and have a right-handed cutting direction. However, it is contemplated that the flutes 16 and 18 could follow a left-handed twist and that the cutting edges 20 and 22 would have a left-handed cutting direction.

As mentioned above, the cutting edges 20 and 22 are generally directed upwardly or away from the tapered end 14 of the shank 12. To this end, each of the first and second flutes 16 and 18 is undercut. The first flute 16 is undercut in the region, generally denoted as the numeral 30, immediately adjacent the cutting edge 20 to form what is sometimes referred to as a positive rake angle flute. The second flute 18 is also undercut in the region generally denoted as the numeral 32, immediately adjacent the second cutting edge 22 to form the positive rake angle flute.

With particular attention to FIG. 2, the first and second flutes 16 and 18 cooperate to define a web area 34 therebetween. The web area 34 has a continuous radial web clearance from the first cutting edge 20, generally denoted by the numeral 36A, and a continuous radial web clearance, generally denoted as the numeral 36B, from the second cutting edge 22.

As can be best seen in FIGS. 1 and 2, the wall 38 of the web 34 formed by the first flute 16 slopes away from the first cutting edge 20 generally inwardly of the shank 12 in a direction toward the tapered end 14 of the shank 12. As illustrated, the wall 38 immediately slopes away from the cutting edge 20. Similarly, the wall 40 of the web 34 formed by the second flute 18 slopes away from the second cutting edge 22 generally inwardly of the shank 12 in a direction toward the tapered end 14 of the shank 12. As illustrated, the wall 40 immediately slopes away from the cutting edge 22.

The first cutting edge 20 is defined by the undercut region 30 and the sloping wall 38 of the web 34 and is, thus, a very sharp edge with minimal or virtually no land area about the outside circumference of the first cutting edge 20. The second cutting edge 22 is also similarly defined by the undercut region 32 and the sloping wall 40 of the web 34 and is, thus, a very sharp edge with a minimal or virtually no land area about the outside circumference of the second cutting edge 22.

Referring to FIG. 1, the end of the cylindrical portion of the shank 12 above the tapered length 13 is illustrated as being formed with two notches 42 so that the dental file can be adapted for use in a power driven dental drill apparatus or hand piece. Alternatively, a handle 44 is adapted to be attached to the cylindrical end of the shank 12 so that the file 10 can be used manually.

A better understanding of the shortcomings of the heretofore known dental files will be had by referring to FIG. 5 during the following discussion. FIG. 5 illustrates a heretofore known dental file 46 in use in a curved root canal 48. As illustrated, the heretofore known dental file 46 has a shank 50 terminating at an end 51, a working or cutting surface 52 formed in the shank 50 for cutting tissue from the root canal 48, and manipulating means 56 at the other end of the shank.

As was generally discussed above, as the dental file 46 is moved in the curved root canal a force is exerted on the shank 50 near it's end 51 by the tooth structure within the curved root canal 48 and on the manipulating means 56 by the operator. These forces create a force couple which bends the shank into an arcuate configuration generally conforming to the curvature of the root canal 48. The component of the shank bending couple exerted on the shank is applied against the working surface 52 near the end 51 of the file shank and is denoted as force vector "A". The component of the shank bending couple exerted on the manipulating end 56 by the operator is a secondary force couple denoted by the force vectors "B".

Because of the modulus of elasticity of the material from which the file shank is fabricated, the file shank 50 will exert an equal and opposite force, denoted as force vector "C", to the force vector "A" against the concave wall of the curved root canal 48. This counter-force "C" will force the cutting surface 52 near the end 51 of the shank 50 against the concave wall of the root canal and increase the cutting action of the cutting surface 52 of the file shank against the concave wall of the curved root canal. Heretofore known dental files could, therefore, cut too deeply into the concave wall creating a slit or ledge denoted as the letter "D". As the ledge becomes deeper with succeeding larger files, it could even perforate the tooth structure. As succeedingly larger diameter files are used, there is a danger of penetrating through the apical foramen, denoted by the letter "E", of the root canal increasing the size of the apical foramen "E" causing undue damage to the tooth structure and injury to the tooth supporting tissue.

Figure 6:
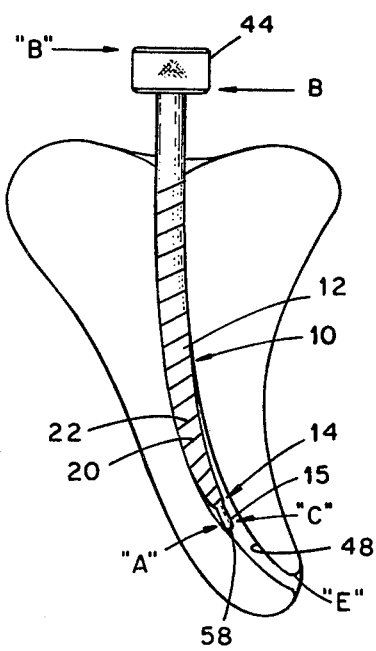
FIG. 6 illustrates the file of FIG. 1 in use.
Figure 7:
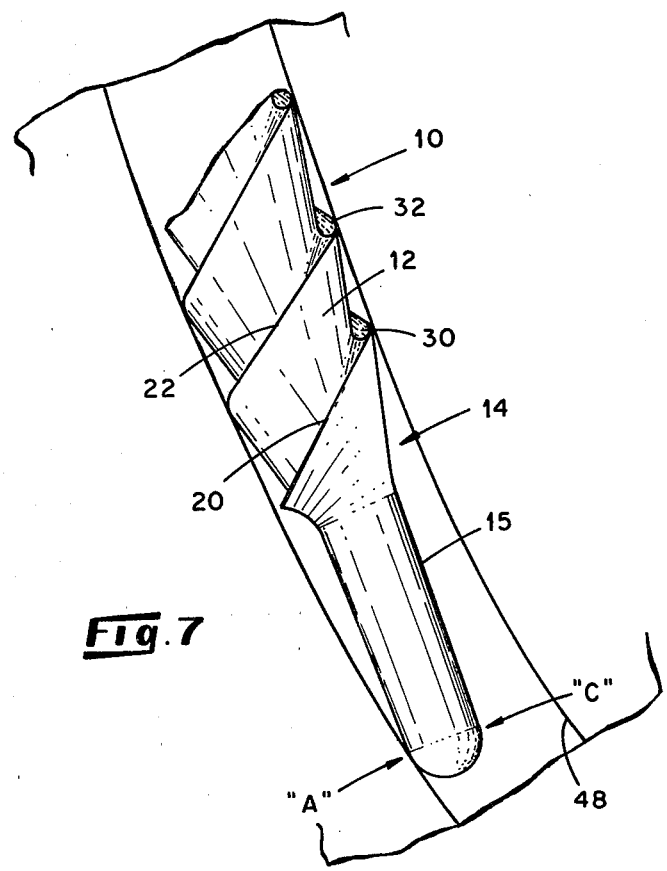
FIG. 7 is an enlarged view of the end portion of the file of FIG. 4 in use; and, FIG. 8 diagramatically illustrates a root canal cleaned by a set of files of the present invention.

Returning to a discussion of the present invention, with reference to FIGS. 1, 3, 4, 6 and 7, the pilot 15 has a generally cylindrical smooth wall and is integrally formed with and coaxially projects from the tapered end 14 of the shank 12. The end 58 of the pilot 15 has no surfaces capable of cutting and is illustrated as being rounded so that the pilot 15 will not dig into or otherwise cut the tooth structure surrounding the curved root canal 48. It should be clearly understood that other blunt shapes will also work. The pilot 15 is sized so that it will contact the concave wall of a curved root canal 48 before the cutting edges 20 and 22 near the tapered end 14 of the shank 12 adjacent the pilot 15 contact the concave wall of the root canal 48 (as can be seen in FIGS. 6 and 7). Thus, the pilot 15 guides the fluted length 13 of the shank along the curved path of the curved root canal 48 and relieves the cutting edges 20 and 22 near the end 14 of the shank 12 adjacent the pilot 15 of the force exerted by the wall of the root canal which causes the shank 12 to bend. The relative sizing of the pilot 15 and tapered end 14 of the shank results in the force vector "A" applied to the shank 12 being exerted on the pilot 15 and not on the cutting edges 20 and 22 of the shank near the end of the shank. Therefore, the equal and opposite force "C" will be applied by the pilot 15 against the concave wall of the root canal 48. To this end, it has been found that for dental files 10 having a shank diameter, measured at about 1 mm above the tapered end 14, of from about 0.30 mm to about 0.40 mm, the pilot 15 should have a diameter of about 0.25 mm and a length greater than about 1 mm and less than about 3 mm measured to the first cutting edge 20 and 22 adjacent the tapered end 14. For dental files 10 having a diameter, measured at about 1 mm above the tapered end 14, of from about 0.45 mm and larger, the pilot 15 should have a diameter of about 0.35 mm and a length greater than about 1 mm and less than about 3 mm measured from the first cutting edge 20 and 22 adjacent the tapered end 14.

The present invention also provides a set of files 10, as described above, comprising a first plurality of files 10 having tapered shanks 12 which incrementally increase in diameter from one file to the next larger file with the dimensions of the pilot 15 being substantially the same for each file of the first plurality of files, and a second plurality of files having tapered shanks 12 which incrementally increase in diameter from one file to the next larger file with the dimensions of the pilot 15 being substantially the same for each file of the second plurality of files. The smallest file (see FIG. 4) of the second plurality of files is larger in diameter than the largest file (see FIG. 3) of the first plurality. The pilot 15 of the second plurality of files is larger in diameter than the pilot 15 of the first plurality of files. Preferably, the diameter of the pilot 15 of the second plurality of files is smaller in diameter than the diameter of the shank 12 of the largest file of the first plurality of files as measured at about 1 mm above the tapered end 14 of the largest file of the first plurality of files. Preferably, however, the pilots of the second plurality of files are of substantially the same length as the pilots of the first plurality of files.

It has been determined that a preferred set of dental files have the following dimensions:

| Fluted Length of Shank | Diam. of Shank 1mm Above Tapered End | Diam. of Shank 14mm Above Tapered End | Length of Pilot | Diam. of Pilot |
|---|---|---|---|---|
| FIRST PLURALITY OF FILES | | | | |
| 16mm | .30mm | .58mm | greater than 1mm to about 3mm | .25mm |
| 16mm | .35mm | .63mm | greater than 1mm to about 3mm | .25mm |
| 16mm | .40mm | .68mm | greater than 1mm to about 3mm | .25mm |
| SECOND PLURALITY OF FILES | | | | |
| 16mm | .45mm | .73mm | greater than 1mm to about 3mm | .35mm |
| 16mm | .50mm | .78mm | greater than 1mm to about 3mm | .35mm |
| 16mm | .55mm | .83mm | greater than 1mm to about 3mm | .35mm |
| 16mm | .60mm | .88mm | greater than 1mm to about 3mm | .35mm |
| 16mm | .65mm | .93mm | greater than 1mm to about 3mm | .35mm |
| 16mm | .70mm | .98mm | greater than 1mm to about 3mm | .35mm |
| 16mm | .75mm | 1.03mm | greater than 1mm to about 3mm | .35mm |
| 16mm | .80mm | 1.08mm | greater than 1mm to about 3mm | .35mm |

For the reason that the bending force vector "A" is exerted on the pilot 15 and not on the fluted cutting edges 20 and 22 near the end 14 of the shank 12, the operator can selectively increase the curvature of the bend in the shank 12 by manually increasing the magnitude of the secondary force couple "B" at the handle 44 or powered handpiece to lead the file into a portion of the curved root canal which may have a diminishing radius of curvature.

Typically, the procedure for preparing a root canal for filling involves the use of a set of dental files having progressively larger diameters. The smallest dental file is used to cut an initial path through the tissue to be removed from the root canal and incrementally larger diameter files are used in succession to progressively remove more of the tissue until all of the dead or damaged tissue has been removed from the root canal. In this way, the dentist can check his progress after each cut.

With heretofore known dental files each succeedingly larger dental file does not necessarily follow the curvature of the previously cut path because, as discussed above, the bending forces are exerted on the cutting surfaces near the end of the file and therefore these files have a tendency to cut more deeply into the concave wall than into the convex wall of the curved root canal forming a ledge in the concave wall. Thus, each succeeding file further distorts the curved path of the curved root canal and enlarges the size of the ledge cut into the concave wall of the root canal. These files also progressively enlarge the bottom or apical foramen of the root canal.

Using the set of files 10 of the present invention, there is less danger of forming a ledge in the concave wall of the root canal, and of enlarging the apical foramen of the root canal.

Figure 8:
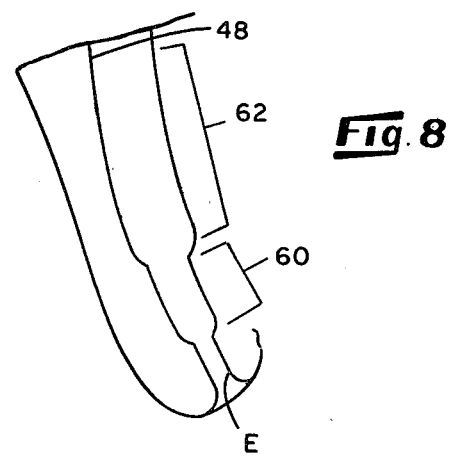

FIG. 8 is an exaggerated diagrammatic illustration of a tooth root canal 48 after the set of files of the present invention have been used. For the reasons previously mentioned, the first plurality of files will follow the path of the curved root canal. The apical foramen "E" is undamaged because, in about 95% of the cases, it is about 0.30 mm in diameter. Therefore, the pilot 15 of the first plurality of files of the set, being preferably 0.25 mm in diameter, will not enlarge it. The area denoted as the numeral 60 is that length of the root canal worked or cleaned by the first plurality of files of the set and corresponds in diameter to the diameter of the shank 12 about 1 mm above the tapered end 14 of the largest file 10 of the first plurality of files, or about 0.40 mm. The area denoted as the numeral 62 is that length of the root canal worked or cleaned by the second plurality of files of the set. Because the pilot 15 of the second plurality of files is larger in diameter than the apical foramen of the root canal, the pilot 15 of the second plurality of files will abut the bottom of the region 60 worked by the first plurality of files. Thus, the second plurality of files is prevented from penetrating and enlarging the apical foramen "E" of the root canal. Also, because the pilot 15 of the second plurality of files is only somewhat smaller in diameter than that of the worked length 60, the pilot 15 of the second plurality of files will easily move into the previously worked length 60, but will not move a significant distance laterally of the worked length 60. Therefore, the pilot 15 of the second plurality of files will guide the files into the worked length 60 faithfully following the path of the first plurality of files.

It should be understood that dental files tapering to a point having cutting surfaces extending to the point can be used in conjunction with the set of files 10 of the present invention if so desired. For example, the initial step of cleaning a root canal could be made with such file having a diameter near the pointed end of less than 0.30 mm, and the set of files 10 of the present invention used to perform the subsequent steps of cleaning the root canal.

The foregoing detailed description is given primarily for clearness of understanding, and no unnecessary limitations should be understood therefrom for modification will be obvious to those skilled in the art upon reading this disclosure and can be made without departing from the spirit of the invention or the scope of the appended claims.

What is claimed is:

1. A set of dental files comprising individual files each having a shank tapered along at least part of its length, having cutting means formed in at least a portion of the tapered length of the shank, the files of the set having tapered shanks which incrementally increase in diameter from one file to the next larger file of the set, and each file of the set comprises a generally cylindrical smooth walled pilot having a generally non-cutting end formed at and projecting coaxially from the tapered end of the shank, the diameter of said pilot being substantially the same for all files of the set and corresponds to a pilot dimensioned for the smallest file of the set said pilot having a length from greater than about 1.0 mm to about 3.0 mm.

2. The set of dental files of claim 1, wherein the pilot of each file of the set has a smaller diameter than the diameter of the tapered shank of the smallest file of the set measured at about 1 mm above the tapered end of the shank.

3. The set of dental files of claim 1, comprising: a first plurality of dental files having said tapered shanks which incrementally increase in diameter from one file to the next larger file of the first plurality of files, each file of said first plurality of files having a pilot of substantially the same diameter and corresponding to the pilot dimensioned for the smallest file of the set; and, a second plurality of dental files having said tapered shanks which incrementally increase in diameter from one file to the next larger file of the second plurality of files, the smallest file of said second plurality of files having a shank diameter larger than the largest file of said first plurality of files, each file of said second plurality of files having a pilot of substantially the same diameter as the rest of the files of said second plurality of files, said diameter being smaller than the diameter of the shank of the largest dental file of said first plurality of files as measured about 1 mm from the tapered end of the largest file of said first plurality of files.

4. The set of dental files of claim 3, wherein the length of said pilot of each file of said second plurality of files is substantially the same as the length of said pilot of each file of said first plurality of files.

* * * * *